(12) United States Patent
Taskinen et al.

(10) Patent No.: US 9,724,004 B2
(45) Date of Patent: Aug. 8, 2017

(54) METHOD AND DEVICE FOR MEASURING TISSUE PRESSURE

(75) Inventors: Tapani Taskinen, Espoo (FI); Aki Backman, Altdorf (DE)

(73) Assignee: HLD HEALTHY LIFE DEVICES OY, Espoo (FI)

( * ) Notice: Subject to any disclaimer, the term of this patent is extended or adjusted under 35 U.S.C. 154(b) by 135 days.

(21) Appl. No.: 13/575,740

(22) PCT Filed: Jan. 28, 2011

(86) PCT No.: PCT/FI2011/050068
§ 371 (c)(1),
(2), (4) Date: Sep. 17, 2012

(87) PCT Pub. No.: WO2011/092379
PCT Pub. Date: Aug. 4, 2011

(65) Prior Publication Data
US 2013/0245454 A1 Sep. 19, 2013

(30) Foreign Application Priority Data
Jan. 29, 2010 (FI) ..................................... 20105077

(51) Int. Cl.
*A61B 5/03* (2006.01)
*A61B 5/00* (2006.01)

(52) U.S. Cl.
CPC .............. *A61B 5/03* (2013.01); *A61B 5/0055* (2013.01); *A61B 5/441* (2013.01); *A61B 5/4878* (2013.01)

(58) Field of Classification Search
USPC ......................................... 600/437, 438, 473
See application file for complete search history.

(56) References Cited

U.S. PATENT DOCUMENTS

| 5,484,399 A | 1/1996 | DiResta et al. |
| 5,524,636 A * | 6/1996 | Sarvazyan ........... A61B 1/0052 600/587 |
| 5,891,065 A * | 4/1999 | Cariapa et al. ............... 601/152 |
| 6,186,962 B1 | 2/2001 | Lloyd et al. |
| 2007/0027411 A1 | 2/2007 | Ella et al. |
| 2008/0200778 A1* | 8/2008 | Taskinen et al. ............. 600/306 |
| 2008/0234607 A1* | 9/2008 | Hunter-Jones et al. ...... 600/587 |
| 2009/0088823 A1 | 4/2009 | Barak et al. |

(Continued)

FOREIGN PATENT DOCUMENTS

| FI | 109651 B | 9/2002 |
| WO | 2007/113755 A2 | 10/2007 |

(Continued)

OTHER PUBLICATIONS

Hendriks F M et al, "Influence of Hydration and Experimental Length Scale on the Mechanical Response of Human Skin" Skin Research and Technology, Munksgaard, Copenhagen, DK, vol. 10, No. 4 (Nov. 1, 2004).

(Continued)

*Primary Examiner* — Rochelle Turchen
(74) *Attorney, Agent, or Firm* — Thompson Hine LLP

(57) ABSTRACT

The method facilitates measuring of a tissue pressure non-invasively utilizing a negative pressure. The device has a pressure chamber, pressure sensor for measuring the pressure in the pressure chamber and a range sensor for measuring the skin tissue rising caused by the negative pressure.

8 Claims, 3 Drawing Sheets

(56) References Cited

U.S. PATENT DOCUMENTS

| | | | |
|---|---|---|---|
| 2009/0118615 A1* | 5/2009 | Kato et al. ................... | 600/438 |
| 2009/0318834 A1* | 12/2009 | Fujiwara et al. ............. | 600/583 |
| 2010/0049447 A1* | 2/2010 | Peyman .............. | G06F 19/3437 |
| | | | 702/19 |
| 2010/0172567 A1* | 7/2010 | Prokoski .............. | A61B 5/0064 |
| | | | 382/132 |

FOREIGN PATENT DOCUMENTS

| | | |
|---|---|---|
| WO | 2009027898 | 3/2009 |
| WO | 2009/098696 | 8/2009 |

OTHER PUBLICATIONS

PCT, International Search Report, International Application No. PCT/FI2011/050068, 5 pages, May 5, 2011.
PCT, International Preliminary Report on Patentability, International Application No. PCT/FI2011/050068, 6 pages, Jul. 31, 2012.

* cited by examiner

METHOD AND DEVICE FOR MEASURING TISSUE PRESSURE

PRIOR APPLICATIONS

This is a US national phase patent application that claims priority from PCT/FI2011/050068 filed 28 Jan. 2011, that claims priority from Finnish Patent Application No. 20105077, filed 29 Jan. 2010.

FIELD OF THE INVENTION

The invention generally relates to measuring tissue pressure. Particularly the invention relates to measuring the pressure in tissue with edema using a measuring device based upon negative pressure.

BACKGROUND AND SUMMARY OF THE INVENTION

Edema in a tissue, for instance lymphoedema, vein-related edema or also edemas born in muscle injuries are a problem that usually is treated by using compression products such as compression stockings or compression gloves. In dimensioning the compression products, determining a suitable compression pressure is a problem.

One method to measure an edema is based upon palpating by hand or fingers and measuring with a tape measure. In some measuring devices based upon state of the art, pressure is applied upon the tissue with a mechanical presser, whereupon the mechanically produced force is measured and the change in the edema or the edema pressure is calculated based upon this. In some, the solutions based upon state of the art are bio-impedance-based devices for measuring the tissue fluid status as well as invasive pressure probes to be inserted into the tissue.

In the U.S. Pat. No. 5,484,399 there is presented a method and device for reducing tissue pressure. The device also comprises a tissue pressure meter. The device has needle-like, long tubes, in the sharp end of which there is at least one hole.

The device is pushed into the tissue and air is sucked from the tubes, whereupon the fluid pressure in the tissue exceeds the pressure in the pipe. Thus fluid is transferred from the tissue into the tube and the pressure in the tissue decreases. The tissue pressure meter is situated in one of the tubes.

In the FI patent 109651 there is presented a method for measuring tissue pressure. In the method an electromagnetic sensor is attached upon the surface of the skin, whereupon the capacitance of the sensor is proportionate to the dielectric constant of the skin and the subcutaneous tissue, which in its turn is proportionate to the water content of the skin. The edema is determined by measuring the capacitance of the electromagnetic sensor at a high frequency, such as 20-500 MHz.

In the U.S. Pat. No. 6,186,962 there are presented methods and devices for measuring tissue pressure. In one device according to the invention there is a platy component, which is attached to the tissue. In the disc there is an aperture for a rod, which is pushed towards the tissue, whereupon the tissue pressure is deducted from the forces directed to the rod.

The above presented measuring methods of the devices according to the state of the art include uncertainty factors, such as the interface between the skin and the electromagnetic sensor and the natural fluctuation in tissue water content. In addition, measurements may be extremely uncomfortable for the patient, as for instance the mentioned invasive methods.

The aim of the present invention is to offer a method and a device for defining tissue pressure in a non-invasive way, utilizing the tissue's own pressure and elasticity.

Characteristic for the tissue measuring device according to the invention is that the device comprises a pressure chamber, means for measuring the pressure in the pressure chamber and means for measuring the rising of the skin tissue caused by the negative pressure.

A device according to an embodiment comprises in addition a CPU, which comprises the means for processing and saving data.

A device according to a second embodiment comprises in addition a pressurization unit, which has been arranged in order to achieve negative pressure in the pressure chamber.

A device according to a third embodiment comprises in addition means for determining tissue pressure by means of the measured skin tissue rising and the measured pressure in the pressure chamber. The measured skin tissue rising and/or the pressure chamber pressure can also be measured as a function of time in order to determine tissue pressure.

In a device according to a fourth embodiment, the means for measuring the rising in skin tissue comprises at least one range sensor. The range sensor may for instance be an infrared sensor, a laser sensor or a tonometer. The device may in addition have means for measuring blood pressure and/or imaging subcutaneous tissues.

The tissue pressure measuring method according to the invention is characterized in that the method comprises the stages in order to create a negative pressure on the tissue surface, to measure the said negative pressure, to measure the tissue rising caused by the negative pressure, and to determine the tissue pressure on the basis of the measured negative pressure and the measured tissue rising.

In an embodiment of the method the negative pressure and/or the tissue rising is measured as a function of time in order to determine tissue pressure.

An advantage with the method lies in that it is non-invasive and that no electrical current or magnetic field is introduced into the tissue. There is created a negative pressure on the skin or tissue surface, whereby the own internal pressure in the tissue and the elastic properties of the tissue are utilized. It is also possible to utilize positive pressure or a combination of positive pressure and negative pressure in the measurement.

BRIEF DESCRIPTION OF THE DRAWINGS

In the following the invention is described in more detail with reference to the advantageous embodiments presented as examples and the attached figures, where.

DETAILED DESCRIPTION

Figure 1:
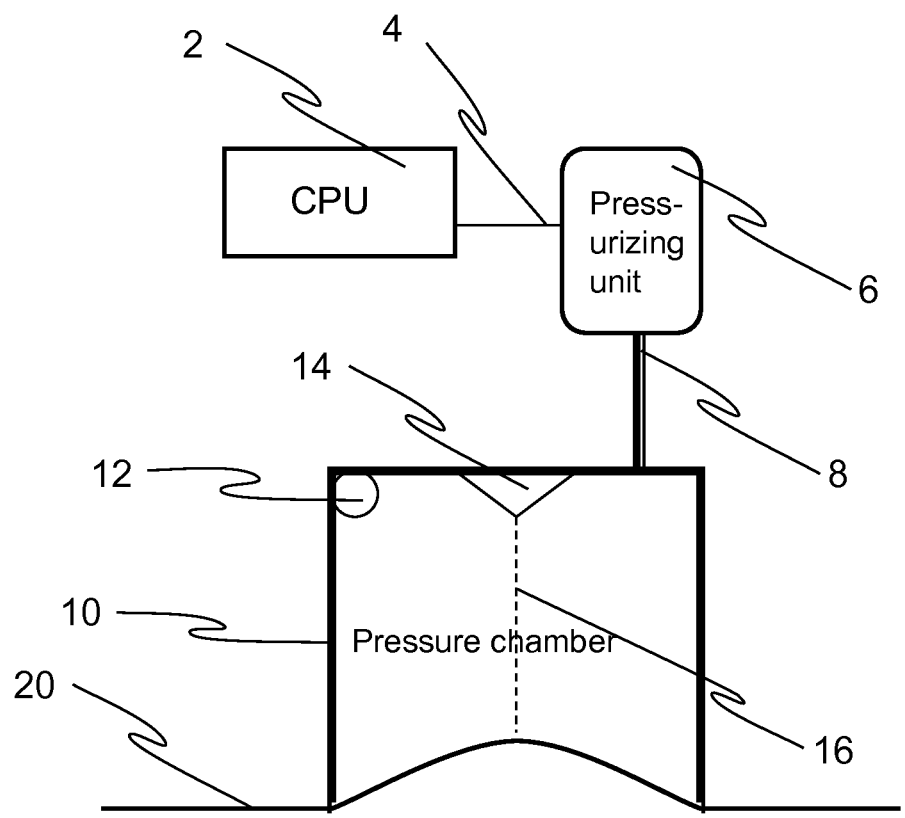
FIG. 1 shows a measuring device according to a simple embodiment.

In FIG. 1 there is presented a measuring device for measuring tissue pressure according to a simple embodiment. The measuring device according to the embodiment comprises a CPU 2, a pressurizing unit 6 and a pressure chamber 10. In connection with the pressure chamber 10 there is, in addition, a pressure sensor 12 and a range sensor 14. The range sensor 14 may for instance be a transceiver operating on infrared, visible light, laser or radio frequencies or a tonometer, having a mechanically protruding part, the movement of which is measured in order to measure the range 16. There may be several pressure sensors and/or range sensors.

The CPU 2 comprises means to process and save data and run software. The CPU 2 is connected to the pressurizing unit 6, which in its turn is connected to the pressure chamber 10. The pressurizing unit 6 is arranged to create a negative pressure in the pressure chamber 10 by removing media, for instance air or water, from the pressure chamber in order to achieve a rising in the tissue 20.

Because of the negative pressure formed in the pressurizing unit 10, the internal pressure in the inter-tissue/intercellular space, in the blood vessels and the lymphatic vessels expands tissue volume and stretches and/or raises the skin, which is elastic. At first, the tissue pressure in the expanded point is lower than in the surrounding tissue space. The inter-tissue fluid/interstitial fluid, the blood and the lymph are transferred from the higher pressure towards the lower pressure and fill up the expanded volume. Thus the skin rises until equilibrium finally is reached because of the elastic force of the tissue. In the state of equilibrium, the forces caused by the elasticity of the tissue and the air pressure in the pressure chamber are of the same magnitude as the force of the tissue pressure.

In the above mentioned event, the pressure and the pressure change can, based upon the signal given by the pressure sensor 12, be measured as a function of time and likewise, based upon the measurements of the range sensor 14, the rising of the tissue and/or skin is known as a function of time. The results of the measurements are transferred to the CPU 2, where the data is saved and processed. Based upon these measurements, the CPU calculates the elastic force of the skin and/or the tissue and further the pressure or edema pressure of the skin and/or the tissue.

Figure 2:
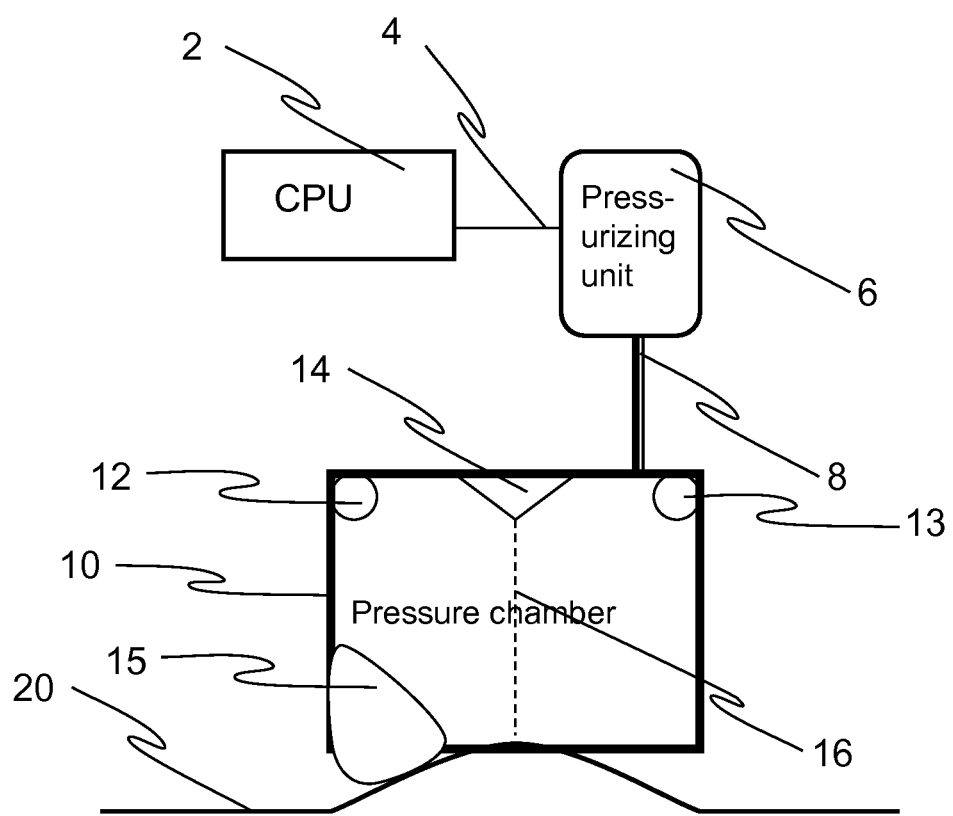
FIG. 2 shows a measuring device according to a more versatile embodiment.

In FIG. 2 there is shown a measuring device for measuring tissue pressure according to a more versatile embodiment. The measuring device of this embodiment comprises more sensors and/or measuring devices than the aforementioned measuring device of a simple embodiment. The range sensor 14 may for instance be a transceiver operating on infrared, visible light, laser or radio frequencies or a tonometer, having a mechanically protruding part, the movement of which is measured in order to measure the range 16. There may be several pressure sensors and/or range sensors. In addition, the pressure sensor or other sensor 13 may be used for measuring the force, wherewith the pressure chamber or other component of the measuring device is pressed against the skin. Thus the friction between the skin and the part of the measuring device facing the skin may be controlled.

The device according to the embodiment may in addition comprise devices 15 for measuring and/or imaging properties of the skin or the subcutaneous tissue. The imaging may take place for instance by ultrasonic, infrared, X-ray and/or any other medically used imaging method. The properties to be measured may for instance be blood pressure, skin temperature, the temperature of the subcutaneous tissues. By subcutaneous tissues is meant one or several of all the tissues under the skin, such as fatty tissue, muscles, bones, tendons etc. The mentioned devices 15 may be situated in- or outside of the pressure chamber 10 and, in addition, in the case of several devices 15 both in- and outside. The obtained measuring results may used as aids in calculating edema pressure.

Figure 3:
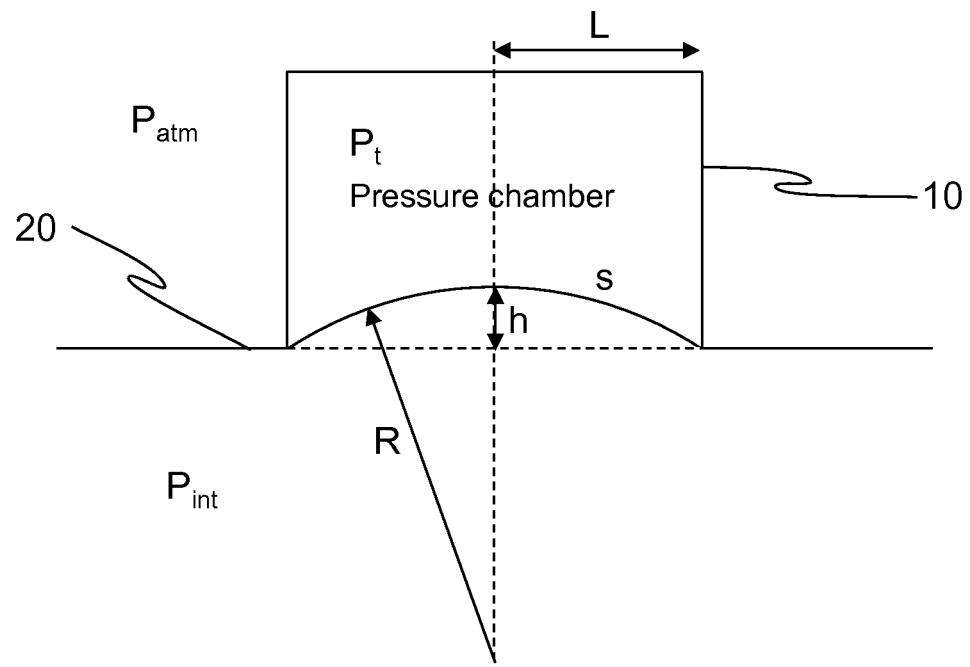
FIG. 3 shows the geometry of a measuring device according to an embodiment, and FIG. 4 visualizes the relationship between skin rising and the negative pressure in use.

In an exemplary embodiment for calculating edema pressure, there are used equations, which are based upon a simplified 2D model under the standard pressure acting in the normal direction of the skin. This is a classic "velaria" problem, where elastic material is used. In FIG. 3 there is shown a visualizing image of the situation and the variables used in the equation. In the equation it is assumed that the total rising h of the raised skin is smaller than the radius of the pressure chamber (h<L). It is assumed that the edge of the pressure chamber that is placed towards the skin is circular, in which case the skin rising determined by the edge can be assumed to be shaped as the calotte of a ball with a radius R, as can be seen from the cross section shown in FIG. 3.

Figure 4:
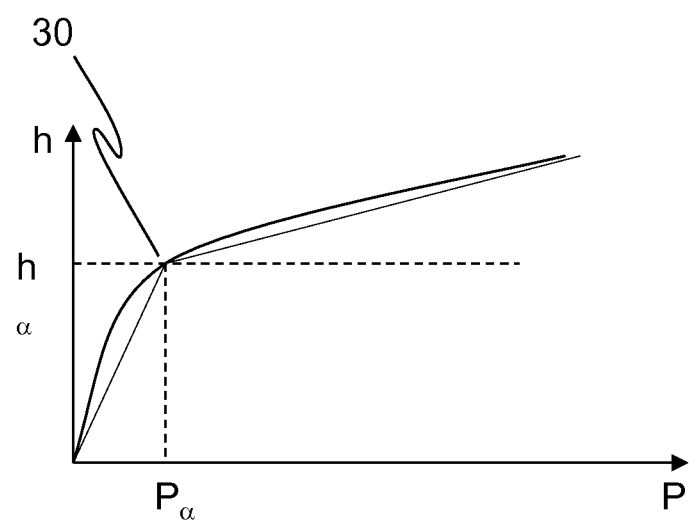

The following values are determined:

$$\Delta P_0 = P_{int} - P_{atm}, \Delta P_t = P_{atm} - P_t$$

$$\Delta P = P_{int} - P_t = \Delta P_0 + \Delta P_t \quad (1),$$

where
$P_t$ is the pressure chamber pressure,
$P_{int}$ is the internal tissue pressure, edema pressure
$P_{atm}$ is the ambient air pressure In this embodiment it is assumed that the length of half of the skin under the pressure chamber is L, which is the radius of the pressure chamber aperture towards the skin. In FIG. 4 there is presented the qualitative behaviour of the skin under negative pressure. There are two areas visible in FIG. 4. In the first area there occurs a fast growth of the skin rising, as negative pressure is applied. This goes on until the turning point (30), where the change in question retards and the response starts to saturate. The first area also seems to correspond to a situation, where the "loose" skin around the pressure chamber slides under the negative pressure without the occurrence of any significant elastic elongation. If the friction between the surface of the pressure chamber towards the skin and the skin is big, the skin sliding in question does not necessarily occur at all.

The second area corresponds to skin behaviour, when all possible peripheral loose skin already has been brought under the pressure chamber and the growth of the rising is due to elastic deformation of the skin.

In order to explain the looseness in question, we determine the parameter a, which is the relation between the half-part s of the length of the skin that has been deformed under the pressure chamber and the half-part L of the length of the skin under normal conditions. The value α in question is dependent upon the original subcutaneous pressure and is determined:

$$\alpha(\Delta P_0) = \begin{cases} 1 & \Delta P_0 \geq \Delta P_\alpha \\ \alpha_{max}\left(1 - \frac{\Delta P_0}{\Delta P_\alpha}\right) + \frac{\Delta P_0}{\Delta P_\alpha} & \Delta P_0 \leq \Delta P_\alpha \end{cases}, \quad (2)$$

where:

$$\alpha_{max} = \frac{1}{2}\left(\frac{h_\alpha}{L} + \frac{L}{h_\alpha}\right) a \cos\left(\frac{L^2}{h_\alpha^2 + L^2}\right), \quad (3)$$

and the parameters $h_\alpha$ ja $P_\alpha$ are determined in FIG. 4.

Thus, the half-part of the length of the skin under the pressure chamber as the measuring pressure is applied is:

$$s = L \cdot \alpha \cdot \left(1 + \frac{(\Delta P_0 + \Delta P_t) \cdot R}{k}\right), \quad (4)$$

where k is an elasticity coefficient, obtained by presuming that:

$$F = k\Delta s \quad (5)$$

Because the solution obtained for the skin deformation is based upon the length of the circle circumference, the following equations may be obtained based upon the trigonometry of FIG. 2:

$$R = \frac{h^2 + L^2}{2h} \quad (6)$$

$$s = Ra \, \cos\left(\frac{R-h}{R}\right) \quad (7)$$

By combining the equations (6) and (7) one obtains:

$$s = \frac{h^2 + L^2}{2h} a \, \cos\left(\frac{L^2}{h^2 + L^2}\right) \quad (8)$$

By using the equations (4) and (8), we may thus compile the following equation:

$$\Delta P_0 = k \cdot \left(\frac{1}{L \cdot \alpha} a \, \cos\left(\frac{L^2}{h^2 + L^2}\right) + \frac{2h}{h^2 + L^2}\right) - \Delta P_t \quad (9)$$

The afore presented solution is valid only when $\Delta P_0 \leq \Delta P_\alpha$. The equation (9) is dependent upon α, which also is a function of $\Delta P_0$. Because of this, one may have to solve the equation iteratively by using initial guesses as $\Delta P_0$ values in the equation (2).

In order to calculate edema pressure one may also use other methods than those presented in the aforementioned example.

For professionals in the field it stands clear that the previously presented example embodiments of demonstrational reasons are relatively simple in terms of construction and function. By following the model presented in this patent application it is possible to construct different and even very complex solutions utilizing the patent idea presented in this patent application.

The invention claimed is:

1. A method for measuring a value for a tissue pressure of a tissue comprising:

providing a Central Processing Unit (CPU) in operative engagement with a pressurizing unit that is in operative engagement with a pressure chamber having a pressure sensor and a range sensor, the range sensor being one of a transceiver operating on at least one of infrared, visible light or radio frequencies, a laser sensor, or a tonometer having a mechanically protruding part;

the pressurizing unit creating a negative pressure in the pressure chamber;

the pressure sensor measuring the negative pressure as a function of time and transferring measured information about the negative pressure to the CPU;

the range sensor measuring a distance to the tissue to in turn measure a rising of the tissue caused by the negative pressure as a function of time, the range sensor transferring measured information about the rise caused by the negative pressure to the CPU;

the CPU receiving the measured information about the negative pressure from the pressure sensor and the measured information about the rise from the range sensor; and the CPU using the measured information about the negative pressure and the rise to calculate a value for the tissue pressure;

the calculation of the value for the tissue pressure being calculated iteratively as a function of the pressure chamber pressure, the ambient air pressure, an applied force, an elasticity coefficient and the rising of the tissue.

2. The method of claim 1 wherein the method further comprises the step of the CPU using an iterative calculation to determine an internal pressure.

3. The method of claim 1 wherein the method further comprises the step of measuring rising of the tissue by using an infrared sensor, laser sensor or tonometer.

4. The method of claim 1 wherein the method further comprises the step of the CPU measuring movement of a mechanically protruding part of the range sensor.

5. The method of claim 1 wherein the method further comprises the step of the CPU processing and saving data.

6. The method of claim 1 wherein the method further comprises the step of the pressurizing unit raising the skin to a first rise (hα) and permitting blood and lymph to be transferred from high pressure areas to a lower pressure area to fill up an expanded volume of the raised tissue.

7. The method of claim 1 wherein the method further comprises the step of a force sensor controlling a friction between the tissue and a measuring device facing the tissue.

8. The method of claim 1 wherein the method further comprises the CPU assuming that a total rise (h) is smaller than a radius (L) of a pressure chamber of a measuring device.

* * * * *